United States Patent
Kim

(10) Patent No.: US 8,617,226 B2
(45) Date of Patent: Dec. 31, 2013

(54) SCREW FOR FIXING VERTEBRA

(76) Inventor: Min Seok Kim, Incheon (KR)

( * ) Notice: Subject to any disclaimer, the term of this patent is extended or adjusted under 35 U.S.C. 154(b) by 152 days.

(21) Appl. No.: 13/407,100

(22) Filed: Feb. 28, 2012

(65) Prior Publication Data
US 2012/0197315 A1    Aug. 2, 2012

Related U.S. Application Data

(63) Continuation of application No. PCT/KR2010/000218, filed on Jan. 14, 2010.

(30) Foreign Application Priority Data

Aug. 31, 2009    (KR) .................. 10-2009-0081516

(51) Int. Cl.
*A61B 17/04* (2006.01)
*A61B 17/86* (2006.01)
*A61F 2/08* (2006.01)

(52) U.S. Cl.
USPC .......................................... 606/310; 606/304

(58) Field of Classification Search
USPC ................................................ 606/304, 310
See application file for complete search history.

(56) References Cited

U.S. PATENT DOCUMENTS 6,447,513 B1    9/2002    Griggs
2008/0262495 A1    10/2008    Coati et al.

FOREIGN PATENT DOCUMENTS

EP          0706782 A2        4/1996
KR    1020070087499 A         8/2007

OTHER PUBLICATIONS

International Search Report in corresponding application PCT/KR2010/000218 (WO 2011/025098) dated Aug. 31, 2010.

*Primary Examiner* — Sameh Boles
(74) *Attorney, Agent, or Firm* — Kramer/Amado, P.C.

(57) ABSTRACT

The present invention relates to a screw for fixing vertebra comprising a cage as a prosthesis which can be extended to be protruded beyond an external diameter of a screw, and improving the drawback from detaching from the spine following surgical procedures.

5 Claims, 3 Drawing Sheets

SCREW FOR FIXING VERTEBRA

CROSS REFERENCE TO RELATED APPLICATIONS

This application claims priority to PCT Patent Application No. PCT/KR2010/000218, filed on Jan. 14, 2010, and Korean Patent Application No. 10-2009-0081516, entitled SCREW FOR FIXING VERTEBRA, in the name of MinSeok Kim, the entire disclosures of which are hereby incorporated by reference.

FIELD OF THE INVENTION

The present invention relates to a screw for fixing vertebra, and more specifically to a screw for fixing vertebra which can prevent the screw from separating from a pedicle after surgery by providing a prosthesis that can be expanded in protrusion more than the outer diameter of the screw.

BACKGROUND OF THE INVENTION

In general, spinal diseases include prolapsed intervertebral disk (spinal disk) and spinal scoliosis, and a patient with part of the spine damaged cannot engage in activities necessary for daily life in such a condition. Even if the extent of damage is not so serious, if the damaged part of the spine is pressed or touched by another adjacent part it may cause pain.

Therefore, a patient with part of the spine broken or damaged cannot lead a stable daily life unless the damaged part is corrected by carrying out a surgery for supporting it by using an artificial aid in the damaged part.

Of such spinal diseases, spinal scoliosis is a disease in which vertebrae are bent and twisted. If the spinal scoliosis is left alone, deformation of the spine progresses to eventually bring about serious deformity, followed by complications such as deformation of internal organs.

Such spinal scoliosis can be cured completely by wearing a brace or surgery according to the bent angle of vertebrae.

In the methods of operating on spinal scoliosis, there is a method known as a pedicle screw inserting technique for correcting by inserting screws into bent vertebrae. The pedicle screw inserting technique is a method for helping the spine recover to a normal condition by inserting pedicle screws into bent vertebrae and connecting the pedicle screws with each other using a rod.

The patient leads a life with the pedicle screws transplanted semi-permanently. But the pedicle screws inserted in the human body may be deformed by body activity over time or the screws may separate from the pedicle as the fastening is loosened. A patient with osteoporosis has a higher possibility of the pedicle screw separating from the pedicle due to a low bone density.

SUMMARY OF THE INVENTION

Accordingly, to solve the above problems, it is an object of the present invention to provide a screw for fixing vertebra which can prevent screws from separating from the pedicle after surgery by providing a prosthesis that can be expanded in protrusion more than the outer diameter of the screw.

Another object of the present invention is to provide a screw for fixing vertebrae that can be stably utilized also in vertebrae with a low bone density.

In order to accomplish the foregoing objects, according to an embodiment of the present invention, there is provided a screw for fixing vertebrae including: a screw head with a screw head inserting hole formed therein; a screw body, which is formed monolithically with the screw head, having a screw body inserting hole formed longitudinally therein in communication with the screw head inserting hole, and a screw body screw part formed on the outer circumference thereof; a moving member which is inserted in the screw body inserting hole slidably lengthwise and has a protrusion means protruded through one or more through holes formed on the outer circumference of the screw body, and a moving member screw part formed inside of the screw body; an actuating bolt having an actuating bolt screw part screw-joined with the moving member screw part to be rotatably mounted in the screw head inserting hole; and a stripper bolt which is inserted into the screw head inserting hole to fix a connecting rod arranged on the actuating bolt.

Preferably, the protrusion means is at least one protrusion leg which is extended from the moving member and has elasticity that makes it possible to pass through the through holes.

Preferably, the protrusion means is at least one protrusion pin, one end of which is pivotly connected to a connecting bar extended from the bottom end of the moving member by a joint and the other end of which is passed through the through hole.

Preferably, the protrusion means is protruded outwardly more than the screw body screw part.

Preferably, the actuating bolt head of the actuating bolt is formed concavely so as to contact the outer circumference of the connecting rod.

According to the present invention, it is possible to provide a screw for fixing vertebrae that can maintain the fixed state after surgery more securely than the conventional screw for fixing vertebrae. In particular, the screw for fixing vertebrae of the present invention can also be stably used for patients with osteoporosis related spinal disease.

BRIEF DESCRIPTION OF THE DRAWINGS

The above objects, features and advantages of the present invention will become more apparent to those skilled in the related art in conjunction with the accompanying drawings. In the drawings.

DETAILED DESCRIPTION

Figure 1:
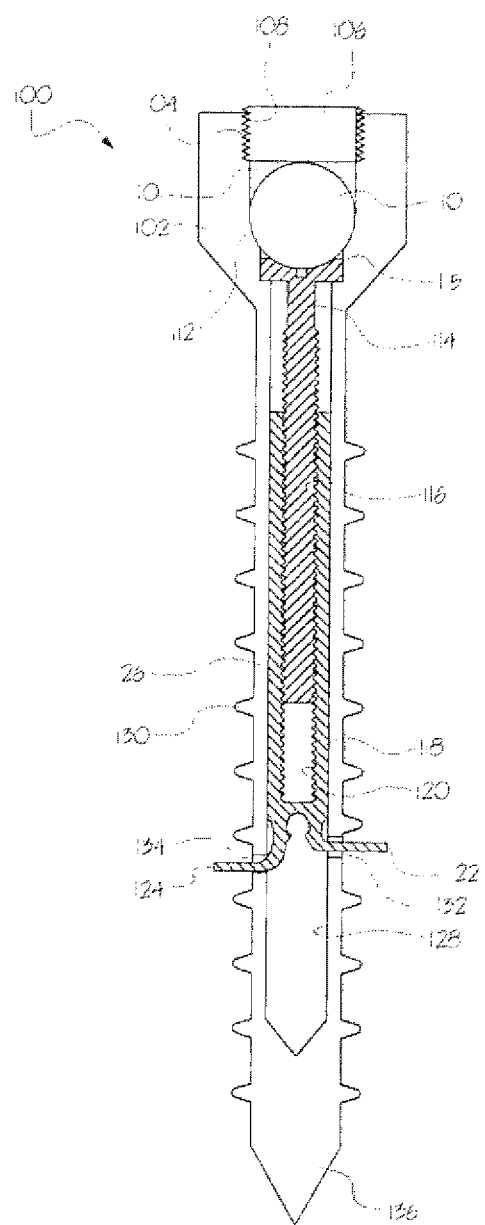
FIG. 1 is a sectional view of a screw for fixing vertebrae according to a first embodiment of the present invention.

Hereinafter, the present invention will be described in detail with reference to the accompanying drawings. When inserting reference numerals into the constituents in the respective drawings, although the constituents are illustrated in different drawings, so far as the constituents are the same, they are described to have the same reference numeral, where possible. The detailed description for the well-known function and constitution, judged to make the gist of the invention obscure, will be omitted.

The screw 100 for fixing vertebrae of the present invention includes a screw head 102 and a screw body 126 that make up the contour. Such a screw 100 for fixing vertebrae may be made of a metal material such as titanium or a polymer material such as PEEK.

Inside the screw body 126 is formed a screw body inserting hole 128, and inside the screw head 102 is formed a screw head inserting hole 101. The screw body inserting hole 128 and the screw head inserting hole 101 are communicated with each other.

On the outer circumference of the screw body 126 is formed a screw body screw part 130, which comes into direct contact with the patient's vertebrae. And a screw front end 136, which is a front end of the screw body 126, is processed into a cone shape so as to be easily inserted into the vertebrae.

And through holes 132 and 134 are formed between screw body screw parts 130 on the outer circumference of the screw body 126. Protrusion legs 122 and 124, which will be described later, are protruded outside from the inside of the screw body 126.

A moving member 118 is inserted in the screw body inserting hole 128, which is an internal space of the screw body 126. The moving member 118 is slidably moved while it is in contact with the inside of the screw body inserting hole 128. The moving member 118 is roughly of a tube shape and has a moving member screw part 120 formed inside. At one end of the moving member 118 are formed protrusion legs 122 and 124 that can be protruded out through the through holes 132 and 134.

Accordingly, since the protrusion legs 122 and 124 should be protruded from the through holes 132 and 134 accordingly as the moving member 118 is moved up and down, it is preferable that the whole of the moving member 118, and at least the protrusion legs 122 and 124, are made of material having elasticity like rubber.

An actuating bolt 114 is fastened to the inside of the moving member 118, and the actuating bolt has an actuating bolt male screw 116 screw-joined with the moving member screw part 120.

In addition, an actuating bolt head 115 of the actuating bolt 114 is rotatably seated on the stepped portion formed in the screw head inserting hole 101 of the screw head 102, as shown in FIG. 1.

Accordingly, if the actuating bolt 114 is rotated, it rotates in its position only, and the rotation of the moving member 118 is prohibited by the protrusion legs 122 and 124, so the moving member 118 moves up and down.

Figure 2:
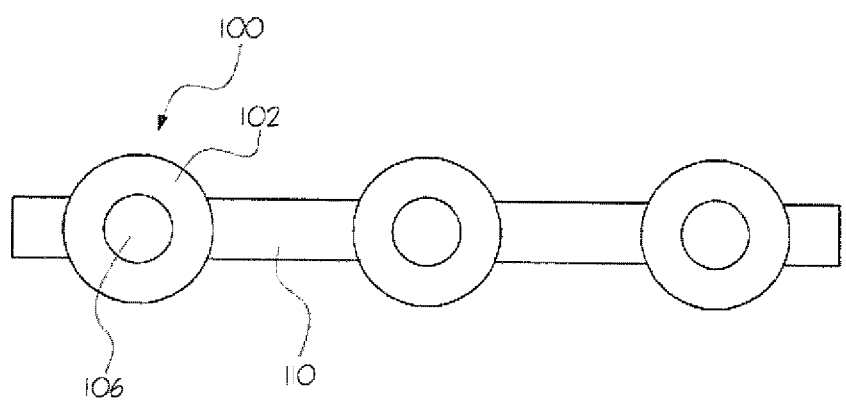
FIG. 2 is a plane view showing a state that the screws for fixing vertebrae of the FIG. 1 are mutually connected by a connecting rod.

And on the actuating bolt 114 is arranged a connecting rod 110 that connects two or more screws 100 for fixing vertebrae as shown in FIG. 2.

The connecting rod 110 is fixed by a stripper bolt 106. The stripper bolt has a stripper bolt male screw 108 to which is screw-joined a screw head female screw 104 formed on the inner circumference of the screw head inserting hole 101, that is, the upper inside of the screw head inserting hole 101.

At this time, the top surface of the actuating bolt head 115 is formed in a concave shape having a radius of curvature the same as the outer circumference of the connecting rod for a secure contact with the connecting rod 110. It is desirable because the area of contact with the connecting rod 110 can be increased as the top surface of the actuating bolt head has a shape corresponding to the inner circumference of the connecting rod 110.

The screw 100 for fixing vertebrae according to the first embodiment of the present invention is constructed basically as mentioned above. Below will be described the method of installing the screw 100 for fixing vertebrae.

First, the initial state of the screw 100 for fixing vertebrae is a state in which the protrusion legs 122 and 124 are hung in the through holes 132 and 134 of the moving member 118 but are not protruded more than the screw body screw part 130. In this case, it is preferable that the moving member 118 is screw-joined with the actuating bolt 114 so as to maintain the initial state.

Next, the screw 100 for fixing vertebrae is inserted and fixed in the necessary position of the spine and the actuating bolt 114 is rotated to move the moving member 118 downward. Accordingly, the protrusion legs 122 and 124 are protruded outwardly more than the screw body screw part 130.

Then, connect the installed screws 100 for fixing vertebrae with each other to the connecting rod 100 and tightly connect the connecting rod 110 by use of the stripper bolt 106.

And apply and solidify cement to fix each of the vertebrae and the screws 100 for fixing vertebrae fixed to the vertebrae.

Figure 3:
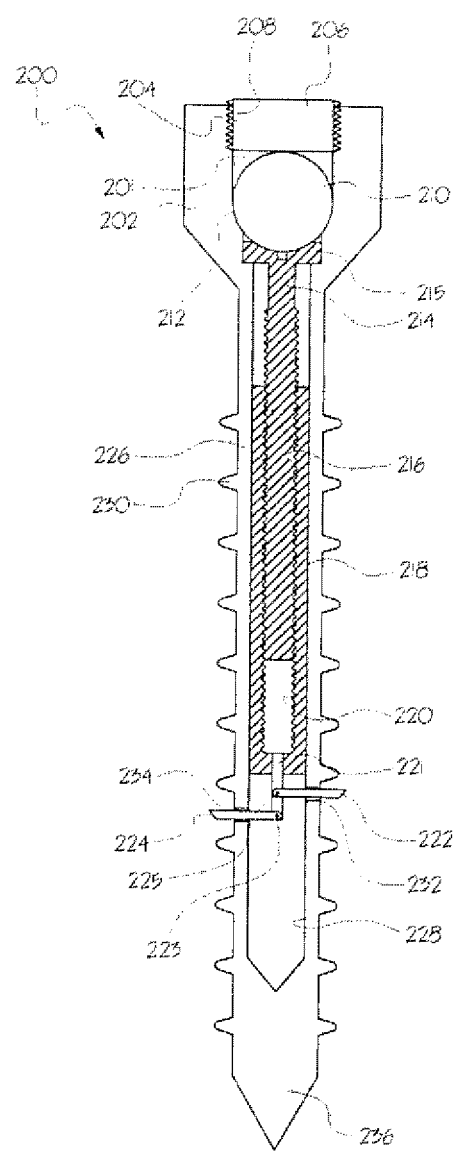
FIG. 3 is a sectional view of a screw for fixing vertebrae according to a second embodiment of the present invention.

Next, a screw 200 for fixing vertebrae according to a second embodiment of the present invention will be described with reference to FIG. 3. Description will be omitted in the second embodiment for the components identical to the first embodiment.

The screw 200 for fixing vertebrae of the second embodiment is different in that it has protrusion pins 222 and 224 instead of the protrusion legs 122 and 124 of the screw 100 for fixing vertebrae of the first embodiment.

The protrusion pins 222 and 224 are pivotly connected to a connecting bar 221 extended from the bottom end of the moving member 218 by joints 223 and 225.

The end portions of the protrusion pins 222 and 224 are inserted in the through holes 232 and 234 in the initial state, so they are not protruded out more than the screw body screw part 230.

When the moving member 218 is moved up and down by the rotation of the actuating bolt 214, the protrusion pins 222 and 224 may be protruded out more than the screw body screw part 230.

At this time, it is preferable that the protrusion pins 222 and 224 are made of a metal material such as titanium.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

The drawings refer to the following items:
  100, 200: Screw for fixing vertebrae
  101, 201: Screw head inserting hole
  102, 202: Screw head, 104, 204: Screw head female screw
  106, 206: Stripper bolt, 108, 208: Stripper bolt male screw
  110, 210: Connecting rod, 112, 212: Connecting rod seat
  114, 214: Actuating bolt, 115, 215: Actuating bolt head
  116, 216: Actuating bolt male screw
  118, 218: Moving member, 120, 220: Moving member screw part
  122, 124: Protrusion leg, 126, 226: Screw body
  128, 218: Screw body inserting hole
  130, 230: Screw body screw part
  132, 134, 232, 234: Through hole
  136, 236: Screw front end, 221: Connecting bar
  222, 224: Protrusion pin, 223, 225: Joint

What is claimed is:

1. A screw for fixing vertebrae comprising:
   a screw head with a screw head inserting hole formed therein;
   a screw body, which is formed monolithically with the screw head, having a screw body inserting hole formed longitudinally therein in communication with the screw head inserting hole, and a screw body screw part formed on the outer circumference thereof;

a moving member which is inserted in the screw body inserting hole slidably lengthwise and has a protrusion means protruded through one or more through holes formed on the outer circumference of the screw body, and a moving member screw part formed inside of the screw body;

an actuating bolt having an actuating bolt screw part screw-joined with the moving member screw part to be rotatably mounted in the screw head inserting hole; and a stripper bolt which is inserted into the screw head inserting hole to fix a connecting rod arranged on the actuating bolt.

2. The screw for fixing vertebrae of claim 1, wherein the protrusion means is at least one protrusion leg which is extended from the moving member and has elasticity that makes it possible to pass through the through holes.

3. The screw for fixing vertebrae of claim 1, wherein the protrusion means is at least one protrusion pin, one end of which is pivotly connected to a connecting bar extended from the bottom end of the moving member by a joint and the other end of which is passed through the through hole.

4. The screw for fixing vertebrae of claim 1, wherein the protrusion means is protruded outwardly more than the screw body screw part.

5. The screw for fixing vertebrae of claim 1, wherein the actuating bolt head of the actuating bolt is formed concavely so as to contact the outer circumference of the connecting rod.

\* \* \* \* \*